(12) United States Patent
Penhasi et al.

(10) Patent No.: US 9,757,338 B2
(45) Date of Patent: Sep. 12, 2017

(54) SUSTAINED-RELEASE DONEPEZIL FORMULATION

(75) Inventors: Adel Penhasi, Holon (IL); Mila Gomberg, Jerusalem (IL)

(73) Assignee: Dexcel Pharma Technologies Ltd., Or Akiva (IL)

( * ) Notice: Subject to any disclaimer, the term of this patent is extended or adjusted under 35 U.S.C. 154(b) by 823 days.

(21) Appl. No.: 13/036,010

(22) Filed: Feb. 28, 2011

(65) Prior Publication Data

US 2011/0237623 A1    Sep. 29, 2011

Related U.S. Application Data

(60) Provisional application No. 61/309,013, filed on Mar. 1, 2010.

(51) Int. Cl.
| | | |
|---|---|---|
| *A61K 9/20* | (2006.01) | |
| *A61K 9/28* | (2006.01) | |
| *A61K 31/445* | (2006.01) | |
| *A61K 47/38* | (2006.01) | |
| *A61K 9/16* | (2006.01) | |
| *A61K 47/32* | (2006.01) | |
| *A61K 47/34* | (2017.01) | |

(52) U.S. Cl.
CPC .......... *A61K 9/1635* (2013.01); *A61K 9/1641* (2013.01); *A61K 9/1652* (2013.01); *A61K 9/205* (2013.01); *A61K 9/2027* (2013.01); *A61K 9/2031* (2013.01); *A61K 9/2846* (2013.01); *A61K 9/2853* (2013.01); *A61K 9/2866* (2013.01); *A61K 31/445* (2013.01); *A61K 47/32* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | |
|---|---|---|
| 4,792,452 A | 12/1988 | Howard |
| 5,126,145 A * | 6/1992 | Evenstad ............ A61K 9/2013 424/465 |
| 5,606,064 A | 2/1997 | Lensky |
| 5,985,864 A | 11/1999 | Imai |
| 6,140,321 A | 10/2000 | Imai |
| 6,245,911 B1 | 6/2001 | Imai |
| 6,287,599 B1 | 9/2001 | Burnside |
| 6,372,760 B1 | 4/2002 | Kato |
| 6,458,807 B1 | 10/2002 | Pratt |
| 6,482,838 B2 | 11/2002 | Pratt |
| 6,576,646 B1 | 6/2003 | Pratt |
| 6,576,677 B1 | 6/2003 | Ukai |
| 6,689,795 B2 | 2/2004 | Pratt |
| 7,160,558 B2 | 1/2007 | Petereit |
| 7,186,842 B2 | 3/2007 | Aher |
| 7,439,365 B2 | 10/2008 | Tarur |
| 7,479,563 B2 | 1/2009 | Imai |
| 7,560,560 B2 | 7/2009 | Parthasaradhi |
| 7,563,808 B2 | 7/2009 | Pratt |
| 7,589,128 B2 | 9/2009 | Szabo |
| 7,592,459 B2 | 9/2009 | Arad |
| 7,727,552 B1 | 6/2010 | Ukai |
| 7,736,672 B2 | 6/2010 | Ray |
| 7,772,399 B2 | 8/2010 | Parthasaradhi Reddy |
| 2001/0031769 A1 | 10/2001 | Jackman |
| 2002/0035128 A1 | 3/2002 | Pratt |
| 2003/0054037 A1 | 3/2003 | Babcock |
| 2003/0104063 A1 | 6/2003 | Babcock |
| 2003/0153598 A1 | 8/2003 | Pratt |
| 2003/0170309 A1 | 9/2003 | Babcock |
| 2003/0203007 A1 | 10/2003 | Ukai |
| 2004/0002517 A1 | 1/2004 | Weisman |
| 2004/0013734 A1 | 1/2004 | Babcock |
| 2004/0034057 A1 | 2/2004 | Imai |
| 2004/0126422 A1 | 7/2004 | Tony Yu |
| 2004/0156905 A1 | 8/2004 | Babcock |
| 2004/0161459 A1 | 8/2004 | Do |
| 2004/0180931 A1 | 9/2004 | Pratt |
| 2004/0214863 A1 | 10/2004 | Pratt |
| 2005/0019393 A1 | 1/2005 | Augsburger |
| 2005/0031546 A1 | 2/2005 | Bartholomaus |
| 2005/0142190 A1 | 6/2005 | Adin |
| 2005/0181060 A1 | 8/2005 | Friesen |

(Continued)

FOREIGN PATENT DOCUMENTS

| | | |
|---|---|---|
| EP | 181197 | 5/1986 |
| EP | 974366 | 1/2000 |

(Continued)

OTHER PUBLICATIONS

Khanvilkar et al., Influence of hydroxypropyl methylcellulose mixture, apparent viscosity, and tablet hardness on drug release using a 2(3) full factorial design, Drug Dev Ind Pharm. May 2002;28(5), printed from http://www.ncbi.nlm.nih.gov/pubmed/12098849, Abstract only.*

Degussa, Drug Delivery Design an Life Cycle Management, Jan. 2005, printed from http://80.241.206.189/en/pharmapolymers/eudragit/basic_information.Par.0003.TRow.0001.TCell.0001.File.tmp/Product_Services%201e.pdf, 12 pages.* www.rxlist.com, Aricept (donepezil hydrochloride) Tablets, Oct. 21, 2008, printed from http://web.archive.org/web/20081021045639/http://www.rxlist.com/aricept-drug.htm, 2 pages.*

Rowe, Hypromellose, Handbook of Pharmaceutical Excipients, 2003, Pharmaceutical Press, 297-300.*

Beringer et al., Remington's Pharmaceutical sciences, Mack Pub., 21st Edition, 2005, pp. 929-932.*

(Continued)

*Primary Examiner* — Gigi Huang
(74) *Attorney, Agent, or Firm* — Roach Brown McCarthy & Gruber, P.C.; Kevin D McCarthy (57) ABSTRACT

A sustained-release formulation for an acetylcholinesterase inhibitor, comprising an acetylcholinesterase inhibitor and at least two gel-forming polymers, and methods of manufacture thereof. The acetylcholinesterase inhibitor preferably comprises donepezil.

8 Claims, 3 Drawing Sheets

(56) References Cited

U.S. PATENT DOCUMENTS

| | | |
|---|---|---|
| 2005/0181062 A1 | 8/2005 | Appel |
| 2005/0232990 A1 | 10/2005 | Boehm |
| 2005/0236741 A1 | 10/2005 | Arkenau |
| 2005/0250812 A1 | 11/2005 | Pratt |
| 2005/0288330 A1 | 12/2005 | Naidu |
| 2006/0002859 A1 | 1/2006 | Arkenau |
| 2006/0122226 A1 | 6/2006 | Adin |
| 2006/0153895 A1 | 7/2006 | Siegel |
| 2006/0159721 A1 | 7/2006 | Siegel |
| 2006/0159753 A1 | 7/2006 | Ueki |
| 2006/0160852 A1 | 7/2006 | Kimura |
| 2006/0183776 A9 | 8/2006 | Pratt |
| 2006/0193782 A1 | 8/2006 | Bartholomaus |
| 2006/0193914 A1 | 8/2006 | Ashworth |
| 2006/0246003 A1 | 11/2006 | Kimura |
| 2006/0280789 A1 | 12/2006 | Ueki |
| 2007/0003616 A1 | 1/2007 | Arkenau-Maric |
| 2007/0048228 A1 | 3/2007 | Arkenau-Maric et al. |
| 2007/0123565 A1 | 5/2007 | Aher |
| 2007/0129402 A1* | 6/2007 | Ueki et al. ............. 514/319 |
| 2007/0148232 A1 | 6/2007 | Crew |
| 2007/0148236 A1 | 6/2007 | Babcock |
| 2007/0183979 A1 | 8/2007 | Arkenau-Maric |
| 2007/0183980 A1 | 8/2007 | Arkenau-Maric |
| 2007/0191610 A1 | 8/2007 | Nagarimadugu |
| 2007/0224260 A1 | 9/2007 | Mehta |
| 2008/0031946 A1 | 2/2008 | Tchoreloff |
| 2008/0063705 A1 | 3/2008 | Vrbinc |
| 2008/0076928 A1 | 3/2008 | Tarur |
| 2008/0114173 A1 | 5/2008 | Mathad |
| 2008/0194827 A1 | 8/2008 | Adin |
| 2008/0213368 A1 | 9/2008 | Ueki |
| 2008/0214557 A1 | 9/2008 | Ueki |
| 2008/0247959 A1 | 10/2008 | Bartholomaus |
| 2008/0248107 A1 | 10/2008 | Pilgaonkar |
| 2008/0292707 A1 | 11/2008 | Babcock |
| 2008/0305140 A1 | 12/2008 | Siegel |
| 2008/0311049 A1 | 12/2008 | Arkenau-Maric |
| 2008/0311187 A1 | 12/2008 | Ashworth |
| 2008/0311202 A1 | 12/2008 | Schulze Nahrup |
| 2008/0312264 A1 | 12/2008 | Arkenau-Maric |
| 2009/0005408 A1 | 1/2009 | Arkenau-Maric |
| 2009/0011024 A1 | 1/2009 | Babcock |
| 2009/0012184 A1 | 1/2009 | Rosenberg |
| 2009/0023778 A1 | 1/2009 | Kimura |
| 2009/0028938 A1 | 1/2009 | Berndl |
| 2009/0060979 A1 | 3/2009 | Bezwada |
| 2009/0098200 A1 | 4/2009 | Temtsin Krayz |
| 2009/0130205 A9 | 5/2009 | Vrbinc |
| 2009/0142404 A1 | 6/2009 | Appel |
| 2009/0187020 A1 | 7/2009 | Pathi |
| 2009/0208579 A1 | 8/2009 | Ueki |
| 2009/0208584 A1 | 8/2009 | Yoshinari |
| 2009/0253746 A1 | 10/2009 | Soldevilla Madrid |
| 2009/0297572 A1 | 12/2009 | Siegel |
| 2009/0298879 A1 | 12/2009 | Krizmanic |
| 2010/0016362 A1 | 1/2010 | Harada |
| 2010/0028440 A1 | 2/2010 | Dobry |
| 2010/0055171 A1 | 3/2010 | Cindric |
| 2010/0105916 A1 | 4/2010 | Kharatkar |
| 2010/0151028 A1 | 6/2010 | Ashworth |
| 2010/0152164 A1 | 6/2010 | Ueki |
| 2010/0159001 A1 | 6/2010 | Cardinal |

FOREIGN PATENT DOCUMENTS

| | | |
|---|---|---|
| EP | 1025858 | 8/2000 |
| EP | 1027886 | 8/2000 |
| EP | 1086706 | 3/2001 |
| EP | 1311272 | 5/2003 |
| EP | 1368007 | 12/2003 |
| EP | 1378238 | 1/2004 |
| EP | 1401503 | 3/2004 |
| EP | 1404302 | 4/2004 |
| EP | 1513528 | 3/2005 |
| EP | 1530457 | 5/2005 |
| EP | 1589950 | 11/2005 |
| EP | 1592399 | 11/2005 |
| EP | 1686966 | 8/2006 |
| EP | 1690528 | 8/2006 |
| EP | 1691787 | 8/2006 |
| EP | 1701703 | 9/2006 |
| EP | 1734934 | 12/2006 |
| EP | 1740156 | 1/2007 |
| EP | 1764101 | 3/2007 |
| EP | 1765298 | 3/2007 |
| EP | 1789020 | 5/2007 |
| EP | 1811957 | 8/2007 |
| EP | 1842533 | 10/2007 |
| EP | 1845945 | 10/2007 |
| EP | 1845956 | 10/2007 |
| EP | 1859789 | 11/2007 |
| EP | 1878444 | 1/2008 |
| EP | 1897558 | 3/2008 |
| EP | 1912626 | 3/2008 |
| EP | 1909689 | 4/2008 |
| EP | 1938842 | 7/2008 |
| EP | 1942875 | 7/2008 |
| EP | 2039349 | 3/2009 |
| EP | 2043610 | 4/2009 |
| EP | 2127651 | 12/2009 |
| EP | 2130538 | 12/2009 |
| EP | 2133078 | 12/2009 |
| EP | 2138177 | 12/2009 |
| EP | 2140868 | 1/2010 |
| EP | 2170291 | 4/2010 |
| EP | 2185130 | 5/2010 |
| EP | 2200588 | 6/2010 |
| IL | 150509 | 7/2007 |
| IL | 151151 | 3/2009 |
| IL | 154711 | 5/2009 |
| IL | 173558 | 2/2012 |
| JP | 11106354 | 4/1999 |
| WO | WO97/46526 | 12/1997 |
| WO | WO98/43675 | 10/1998 |
| WO | WO00/12135 | 3/2000 |
| WO | WO00/59544 | 10/2000 |
| WO | WO01/66114 | 9/2001 |
| WO | WO02/067906 | 9/2002 |
| WO | WO03/000226 | 1/2003 |
| WO | WO03/000238 | 1/2003 |
| WO | WO03/000294 | 1/2003 |
| WO | WO04/000317 | 12/2003 |
| WO | WO2004/014342 | 2/2004 |
| WO | WO2004/060354 | 7/2004 |
| WO | WO2004/071486 | 8/2004 |
| WO | WO/2005/016313 | 2/2005 |
| WO | WO2005/046647 | 5/2005 |
| WO | WO2005/053651 | 6/2005 |
| WO | WO2005/053655 | 6/2005 |
| WO | WO2005/065656 | 7/2005 |
| WO | WO2005/070332 | 8/2005 |
| WO | WO2005/097124 | 10/2005 |
| WO | WO/2005/102286 | 11/2005 |
| WO | WO2005/105054 | 11/2005 |
| WO | WO/2006/002883 | 1/2006 |
| WO | WO2006/024944 | 3/2006 |
| WO | WO2006/045512 | 5/2006 |
| WO | WO2006/070781 | 7/2006 |
| WO | WO/2006/082099 | 8/2006 |
| WO | WO2006/084696 | 8/2006 |
| WO | WO2006/118265 | 11/2006 |
| WO | WO2007/011955 | 1/2007 |
| WO | WO2007/013395 | 2/2007 |
| WO | WO2007/017249 | 2/2007 |
| WO | WO2007/026864 | 3/2007 |
| WO | WO2007/035408 | 3/2007 |
| WO | WO2007/036952 | 4/2007 |
| WO | WO2007/052299 | 5/2007 |
| WO | WO2007/073782 | 7/2007 |
| WO | WO2007/119118 | 10/2007 |
| WO | 2007135408 | 11/2007 |
| WO | WO2008/012617 | 1/2008 |
| WO | WO2009/001146 | 12/2008 |

(56) References Cited

FOREIGN PATENT DOCUMENTS

| WO | WO2009/021656 | 2/2009 |
|----|---------------|--------|
| WO | WO2009/040818 | 4/2009 |
| WO | WO2010/071216 | 6/2010 |
| WO | WO2010/080580 | 7/2010 |

OTHER PUBLICATIONS

Dow Technical Handbook, Methocel Cellulose Ethers, Sep. 2002, Dow Chemical Company, 32 pages.*
Rowe et al., Polyoxymethacrylates, Handbook of Pharmaceutical Excipients, 2006, Pharmaceutical Press, 553-560.*
Search Report for EP 11155954.8 dated Jun. 24, 2011.
Khanvilkar et al., "Influence of Hydroxypropyl Methylcellulose Mixture, Apparent Viscosity, and Tablet Hardness on Drug Release Using a 2(3) Full Factorial Design", Drug Development and Industrial Pharmacy, 28(5), 601-608 (2002)—8 pages.

* cited by examiner

SUSTAINED-RELEASE DONEPEZIL FORMULATION

This application claims priority from U.S. Provisional Application 61/309,013, filed on 1 Mar. 2010, which is hereby incorporated by reference as if fully set forth herein.

FIELD OF THE INVENTION

The present invention relates to a novel formulation for a cholinesterase inhibitor, and methods of preparation thereof, and in particular, to a sustained release formulation comprising an acetylcholinesterase inhibitor such as donepezil and a combination of at least two gel-forming polymers.

BACKGROUND OF THE INVENTION

Acetylcholinesterase inhibitors are agents which inhibit the cholinesterase enzyme from breaking down acetylcholine, thereby increasing both the level and duration of action of the neurotransmitter acetylcholine. Examples of reversible inhibitors of acetylcholinesterase include organophosphates; carbamates; phenanthrene derivatives; piperidine derivatives; tacrine, edrophonium, huperzine A and ladostigil.

Acetylcholinesterase inhibitors are indicated for the management of mild to moderate Alzheimer's disease, which is associated with significant losses in cholinergic neurons and decreased concentrations of acetylcholine, which is significantly involved in learning and memory processes. Acetylcholinesterase inhibitors commonly used in the treatment of Alzheimer's disease include donepezil, rivastigmine and galantamine.

Donepezil ((±)-2,3-dihydro-5,6-dimethoxy-2-[[1-(phenylmethyl)-4-piperidinyl]methyl]-1H-inden-1-one hydrochloride), a piperidine derivative, is a centrally acting reversible acetylcholinesterase inhibitor, used mainly in the treatment of Alzheimer's disease, where it is used to increase cortical acetylcholine. It has an oral bioavailability of about 100%, and easily crosses the blood-brain barrier.

Donepezil is both excreted in the urine intact and extensively metabolized to four major metabolites, two of which are known to be active, and a number of minor metabolites, not all of which have been identified. Donepezil is metabolized by CYP 450 isoenzymes 2D6 and 3A4 and undergoes glucuronidation.

US 20060159753 teaches a sustained release formulation comprising a basic drug, which may be donepezil, and at least one enteric polymer.

U.S. Pat. No. 4,792,452 discloses a controlled-release formulation for a pharmaceutical of basic character comprising a pH-dependent polymer and a pH-independent hydrocarbon gelling agent.

U.S. Pat. No. 6,287,599 teaches sustained release pharmaceutical dosage forms comprising at least one non-pH dependent sustained release agent and at least one pH dependent agent.

US 20060280789 and US 20070129402 teach matrix-type sustained release formulations of basic drugs, including acetylcholinesterase inhibitors, such as donepezil, comprising at least one enteric polymer and optionally at least one water-insoluble polymer.

WO 07/036,952 teaches a sustained release formulation comprising a combination of a non-swelling pH dependent release retardant and a non swelling pH independent release retardant.

Donepezil hydrochloride is currently marketed for oral administration under the trade names ARICPEPT®, by Eisai, in the form of film-coated tablets and orally-disintegrating tablets, comprising 5 or 10 mg of the active ingredient. The tablets provide immediate release of donepezil and are generally administered once a day. Peak plasma concentrations are reached in 3 to 4 hours, causing a sharp spike in the patient's blood plasma levels. The initial spike in blood plasma levels may cause undesirable side effects in patients, such as anxiety, nightmares, insomnia, and/or gastrointestinal problems (e.g., nausea, emesis, diarrhea).

SUMMARY OF THE INVENTION

Sustained-release dosage forms are designed to release a drug at a predetermined rate by maintaining a constant drug level for a specific period of time with minimum side effects.

Compared to immediate release formulations, a sustained release formulation containing a physiologically active drug allows blood concentrations of the drug to be maintained for a long time or above the therapeutic concentration. By providing a sustained-release formulation of an acetylcholinesterase inhibitor, it may be possible to reduce the frequency of administration, while providing the same or better therapeutic effects, potentially improving compliance. The sustained-release formulation may avoid a rapid increase in blood plasma concentration levels immediately after administration of the drug, thus potentially reducing or eliminating adverse side effects.

According to some embodiments of the present invention, there is provided a sustained-release formulation for an acetylcholinesterase inhibitor, comprising an acetylcholinesterase inhibitor and at least two gel-forming polymers.

As used herein, the term "acetylcholinesterase inhibitor" includes acetylcholinesterase inhibitors, stereoisomers of acetylcholinesterase inhibitors, pharmaceutically acceptable salts of acetylcholinesterase inhibitors, and pharmaceutically acceptable salts of stereoisomers of acetylcholinesterase inhibitors.

According to some embodiments, the at least two gel-forming polymers comprise at least one non-ionic gel-forming polymer (such as polyvinylpyrrolidone, polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, acacia, dextrin, starch, polyhydroxyethylmethacrylate, a water-soluble non-ionic polymethacrylate or copolymer thereof, a modified cellulose, a modified polysaccharide, a non-ionic gum, a non-ionic polysaccharide, and mixtures thereof), and at least one anionic gel-forming polymer (such as sodium carboxymethylcellulose; carboxymethyl cellulose; an anionic polysaccharide, such as sodium alginate, alginic acid, pectin, polyglucoronic acid, polygalacturonic acid, chondroitic sulfate, carrageenan, and furcellaran; an anionic gum, such as xanthan gum; a polymer of acrylic acid; a carbomer; a Carbopol® copolymer, such as Carbopol 934, 940, 941 or 974P; a Pemulen® polymer; and polycarbophil); or at least two different non-ionic gel-forming polymers; or at least two non-ionic gel-forming polymers having the same chemistry, but differing in at least one parameter such as solubility, viscosity and molecular weight.

According to a preferred embodiment, the acetylcholinesterase inhibitor comprises a piperidine derivative. Preferably, the piperidine derivative comprises donepezil. As used herein, the term "donepezil" is intended to include pharmaceutically acceptable salts of donepezil, such as donepezil hydrochloride, stereoisomers of donepezil, and pharmaceutically acceptable salts of stereoisomers of donepezil.

According to some embodiments, the formulation further comprises at least one excipient, such as a filler (including lactose, glucose, fructose, sucrose, dicalcium phosphate, a sugar alcohol, corn starch, potato starch, sodium carboxymethycellulose, ethylcellulose and cellulose acetate, an enteric polymer or a mixture thereof), a binder (including polyvinyl pyrrolidone, a copolymer of polyvinyl pyrrolidone and polyvinyl acetate, low molecular weight hydroxypropyl cellulose, low molecular weight hydroxypropyl methylcellulose, low molecular weight carboxy methyl cellulose, ethylcellulose, gelatin polyethylene oxide, acacia, dextrin, magnesium aluminum silicate, starch, and polymethacrylates such as Eudragit NE 30D, Eudragit RL, Eudragit RS, Eudragit E, and polyvinyl acetate, an enteric polymer, or mixtures thereof), a disintegrant (such as low-substituted carboxymethyl cellulose sodium, crospovidone, sodium carboxymethyl starch, cross-linked sodium carboxymethyl cellulose, pregelatinized starch, microcrystalline cellulose, water insoluble starch, calcium carboxymethyl cellulose, low substituted hydroxypropyl cellulose, and magnesium or aluminum silicate, or mixtures thereof) and a glidant (such as magnesium, silicon dioxide, talc, starch, and titanium dioxide), or combinations thereof.

In some embodiments, the filler comprises lactose.

In some embodiments, the disintegrant comprises microcrystalline cellulose.

In some embodiments, the glidant comprises silicon dioxide and magnesium stearate.

According to embodiments of the present invention, there is provided a method for manufacturing a sustained-release formulation comprising an acetylcholinesterase inhibitor and at least two gel-forming polymers, the method comprising mixing the acetylcholinesterase inhibitor with at least one optional excipient and a solvent to form a wet granulate; mixing the wet granulate with the at least two gel-forming polymers, and optional excipients and compressing the mixture to form tablets.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

US 20060246003 and US 20060160852 teach a controlled-release composition comprising at least two anti-dementia drugs, one of which may be donepezil. The composition comprises a sustained-release portion and a quick-release portion. The sustained-release portion comprises at least one selected from non-pH-dependent polymeric substances (preferably water-insoluble polymeric substances) and pH-dependent polymeric substances. Neither of these applications provides actual examples of formulations based on these combinations. Since the weight ratio of the components (especially that of the gel forming polymers) in the final formulation is extremely critical for controlling release, these applications do not disclose in full formulations for achieving the desired release profile.

As used herein the term "about" refers to ±10%.

DESCRIPTION OF THE PREFERRED EMBODIMENTS

The present invention is of a sustained-release formulation, comprising an acetylcholinesterase inhibitor and at least two gel-forming polymers.

The combination of gel-forming polymers used in embodiments of the present invention was found to improve the dissolution profile of acetylcholinesterase inhibitors such as donepezil, thereby reducing the sharp blood plasma increase which occurs with the standard commercial formulation. The polymer combination was found to rapidly form a gel of a suitable consistency to retard the release rate, providing slower, smoother release over a longer time period.

The gel formed by the combination of gel-forming polymers provides controlled release, such that when the formulation is ingested and comes into contact with the gastrointestinal fluids, the polymers nearest the surface hydrate to form a viscous gel layer. Because of the high viscosity, the viscous layer dissolves away only gradually, exposing the material below to the same process. The mass thus dissolves away only slowly, thereby slowly releasing the active ingredient into the gastrointestinal fluids. The combination of at least two gel-forming polymers enables properties of the resultant gel, such as viscosity, to be manipulated in order to provide the desired release profile.

According to some embodiments, the combination of at least two gel-forming polymers may comprise a combination of at least one non-ionic gel-forming polymer and at least one anionic gel-forming polymer; a combination of two different non-ionic gel-forming polymers; or a combination of non-ionic gel-forming polymers of the same chemistry, but having different solubilities and/or viscosities and/or molecular weight (for example a combination of hydroxypropyl methylcellulose of different viscosity grades, such as HPMC K100 and HPMC K15M or HPMC K100M). Non-limiting examples of anionic gel forming polymers which are suitable for use in embodiments of the present invention include sodium carboxymethylcellulose (Na CMC), carboxymethyl cellulose (CMC), anionic polysaccharides such as sodium alginate, alginic acid, pectin, polyglucuronic acid (poly-alpha- and -beta-1,4-glucuronic acid), polygalacturonic acid (pectic acid), chondroitin sulfate, carrageenan, furcellaran, anionic gums such as xanthan gum, polymers of acrylic acid or carbomers (Carbopol® 934, 940, 974P NF), Carbopol® copolymers, a Pemulen® polymer, polycarbophil, and others.

Non-limiting examples of suitable non-ionic gel-forming polymers include Povidone (PVP: polyvinyl pyrrolidone), polyvinyl alcohol, copolymer of PVP and polyvinyl acetate, HPC (hydroxypropyl cellulose), HPMC (hydroxypropyl methylcellulose), hydroxyethyl cellulose, hydroxymethyl cellulose, gelatin, polyethylene oxide, acacia, dextrin, starch, polyhydroxyethylmethacrylate (PHEMA), water soluble nonionic polymethacrylates and their copolymers, modified cellulose, modified polysaccharides, nonionic gums, nonionic polysaccharides and/or mixtures thereof.

In some embodiments, the at least two gel-forming polymers comprise at least two of HPMC K100, HPMC K15M and HPMC K100M as non-ionic gel-forming polymers.

Optionally and preferably, a concentration of HPMC K100 is in the range of from about 1% to about 30% (w/w) of the total formulation; a concentration of HPMC K15M is in the range of from about 1% to about 20% (w/w) of the total formulation; and a concentration of HPMC K100M is in the range of form about 1% to about 10% (w/w) of the total formulation.

More preferably, a concentration of HPMC K100 is in the range of from about 11% to about 19%; a concentration of HPMC K15M is in the range of from about 3% to about 5%, and a concentration of HPMC K100M is in the range of from about 1% to about 5%.

In some embodiments, the at least two gel-forming polymers comprise HPMC K100 and HPMC K100M.

In some embodiments, the at least two gel-forming polymers comprise HPMC K100 and HPMC K15M In some embodiments, the at least two gel-forming polymers comprise Carbopol as anionic gel-forming polymer and at least one of HPMC K100, and HPMC K100M as non-ionic gel-forming polymers.

Optionally and preferably, a concentration of Carbopol is in a range of from about 1% to about 20% (w/w) of the total formulation, more preferably from about 2% to about 15%, and most preferably, around 4.5%. Also preferably, a concentration of HPMC K100 in such embodiments is in the range of from about 1% to about 30%, more preferably from about 5% to about 15%, and most preferably about 13.6%. Also preferably, a concentration of HPMC K100M in such embodiments is in the range of from about 1% to about 10%, more preferably from about 1% to about 5%.

In some embodiments, the at least two gel-forming polymers comprise Carbopol and HPMC K100.

In some embodiments, the at least two gel-forming polymers comprise Carbopol, HPMC K100 and HPMC K100M.

In some embodiments, the at least two gel-forming polymers comprise alginic acid as anionic gel-forming polymer, and at least one of HPMC K100 and HPMC K15M as non-ionic gel forming polymers.

In some embodiments, the at least two gel-forming polymers comprise alginic acid and HPMC K15M.

In some embodiments, the at least two gel-forming polymers comprise alginic acid, HPMC K15M and HPMC K100.

Optionally and preferably, in embodiments comprising HPMC K100, HPMC K15M, and alginic acid, a concentration of alginic acid is in the range of from about 1% to about 30%, more preferably from about 10% to about 20%, and most preferably about 15%. Also optionally, in such embodiments a concentration of HPMC K100 is preferably in the range of from about 1% to about 30%, more preferably from about 11.1% to about 13.3%, most preferably around 12%. Also optionally, in such embodiments a concentration of HPMC K15M is in the range of from about 1% to about 15%, more preferably from about 3.8% to about 4.8%, and most preferably about 4%.

According to some embodiments of the present invention, the acetylcholinesterase inhibitor is a reversible inhibitor comprising a piperidine derivative. Preferably, the acetylcholinesterase inhibitor is donepezil. Optionally and preferably, a concentration of donepezil is in the range of about 10% (w/w) of the total formulation.

The formulation of the present invention may optionally comprise at least one excipient, such as a filler, a binder, a disintegrant, and a glidant.

Examples of suitable fillers include but are not limited to lactose, glucose, fructose, sucrose, dicalcium phosphate, sugar alcohols also known as "sugar polyol" such as sorbitol, manitol, lactitol, xylitol, isomalt, erythritol, and hydrogenated starch hydrolysates (a blend of several sugar alcohols), corn starch, potato starch, sodium carboxymethycellulose, ethylcellulose and cellulose acetate, enteric polymers, or a mixture thereof.

According to some embodiments, the filler comprises lactose.

Examples of suitable binders include but are not limited to water-soluble, hydrophilic polymers, such as Povidone (PVP: polyvinyl pyrrolidone), copovidone (a copolymer of polyvinyl pyrrolidone and polyvinyl acetate), low molecular weight HPC (hydroxypropyl cellulose) low molecular weight HPMC (hydroxypropyl methylcellulose), low molecular weight carboxy methyl cellulose, ethylcellulose, gelatin, polyethylene oxide, acacia, dextrin, magnesium aluminum silicate, starch, and polymethacrylates such as Eudragit NE 30D, Eudragit RL, Eudragit RS, Eudragit E, polyvinyl acetate, and enteric polymers, or mixtures thereof.

Examples of suitable enteric polymers for use as fillers or binders in the formulation of the present invention include hydroxypropyl methylcellulose acetate succinate (also known as hypromellose acetate succinate), cellulose acetate phthalate, hydroxypropyl methyl cellulose phthalate, polyvinyl acetate phthalate, poly(methacrylic acid, methyl methacrylate) 1:1 and poly(methacrylic acid, ethyl acrylate) 1:1, alginic acid, and sodium alginate.

In some embodiments, the binder comprises Povidone, ethylcellulose and HPC. Optionally and preferably, ethylcellulose is present at a concentration of about 25% (w/w) of total formulation, HPC is present at a concentration of from about 3% to about 4% (w/w) of total formulation, and Povidone is present at a concentration of from about 11% to about 13% (w/w) of total formulation.

Examples of suitable disintegrants include but are not limited to low-substituted carboxymethyl cellulose sodium, crospovidone (cross-linked polyvinyl pyrrolidone), sodium carboxymethyl starch (sodium starch glycolate), cross-linked sodium carboxymethyl cellulose (Croscarmellose), pregelatinized starch (starch 1500), microcrystalline cellulose, water insoluble starch, calcium carboxymethyl cellulose, low substituted hydroxypropyl cellulose, and magnesium or aluminum silicate.

According to some embodiments, the disintegrant comprises microcrystalline cellulose, optionally at a concentration in the range of from about 6% to about 13% (w/w) of total formulation.

Examples of suitable glidants include but are not limited to magnesium, silicon dioxide, talc, starch, and titanium dioxide.

According to some embodiments, the glidant comprises silicon dioxide and magnesium stearate. Optionally and preferably, silicon dioxide is present at a concentration in the range of from about 0.1% to about 0.6% (w/w) of total formulation, and magnesium stearate is present at a concentration in the range of from about 0.5% to about 0.6% (w/w) of total formulation.

According to some embodiments, any of the formulations of the present invention optionally and preferably comprise a tablet for oral administration. The tablet is optionally formed by granulating the active ingredient with the optional excipients and compressing the granulation into tablets, as described in detail in the Examples section below.

The present invention thus further provides a method for manufacturing a sustained-release formulation comprising an acetylcholinesterase inhibitor and at least two gel-forming polymers, the method comprising mixing the acetylcholinesterase inhibitor with optional excipients and a solvent to form a wet granulate; mixing the wet granulate with at least two gel-forming polymers, and optional excipients and compressing the mixture to form tablets.

Any of the formulations of the present invention may be used for treating a condition related to decreased cortical acetylcholine, such as, for example, Alzheimer's disease.

According to some embodiments, there is provided a method of increasing cortical acetylcholine, the method comprising administration of any of the formulations of the present invention.

According to some embodiments, there is provided a method of treating a condition related to decreased cortical acetylcholine, such as, for example, Alzheimer's disease, the method comprising administration of any of the formulations of the present invention.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The formulations, methods or uses of the present invention may optionally further comprise one or more additional active ingredient for the treatment of Alzheimer's disease, such as, for example, an acetylcholinesterase inhibitor (including galantamine and/or rivastigmine) and/or an N-methyl-d-aspartate (NMDA) receptor antagonist (including memantine).

According to some embodiments, an additional active ingredient may be co-administered either with the formulation of the present invention, either as a single dosage form or in separate dosage forms, either concurrently or sequentially, wherein the additional active ingredient is administered either before or after the composition of the present invention.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Compositions of the present invention may, if desired, be presented in a pack or dispenser device, such as an FDA approved kit, which may contain one or more dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Examples I-VIIIA

Examples I-VIIIA are based on a combination of an anionic gel-forming polymer (Carbopol) and a non-ionic gel-forming polymer (HPMC) as release-controlling agents.

| Materials | I mg/tab | II mg/tab | III mg/tab | IV mg/tab | V mg/tab | VI mg/tab | VII mg/tab | VIII mg/tab | VIIA mg/tab |
|---|---|---|---|---|---|---|---|---|---|
| Donepezil HCl | 20.00 | 20.00 | 20.00 | 20.00 | 20.00 | 24.6 | 24.6 | 24.6 | 24.6 |
| Lactose | 72.00 | 72.00 | 72.00 | 72.00 | 72.00 | 126.05 | 126.05 | 126.05 | 126.05 |
| Ethylcellulose | 50.00 | 50.00 | 50.00 | 50.00 | 50.00 | | | | |
| Hydroxypropyl Cellulose | 8.00 | 8.00 | 8.00 | 8.00 | 8.00 | 9.20 | 9.20 | 9.20 | 9.20 |
| Povidone K-30 | | | | | | 3.45 | 3.45 | 3.45 | 3.45 |
| Total dry gran. | 150.00 | 150.00 | 150.00 | 150.00 | 150.00 | 163.30 | 163.30 | 163.30 | 163.30 |
| Microcrystalline cellulose | | | | | | 27.50 | 33.30 | 22.5 | 21.0 |
| Lactose | 29.00 | 9.00 | 9.00 | 9.00 | 9.00 | | | | |
| Carbopol | 10.00 | 10.00 | 20.00 | 30.00 | 20.00 | 6.90 | 9.60 | 10.4 | 19.7 |
| HPMC-K100 | 10.00 | 30.00 | 20.00 | 10.00 | 10.00 | 29.90 | 31.20 | 31.2 | 23.2 |
| HPMC-K100M | | | | | 10.00 | | | | |

-continued

| Materials | I mg/tab | II mg/tab | III mg/tab | IV mg/tab | V mg/tab | VI mg/tab | VII mg/tab | VIII mg/tab | VIIA mg/tab |
|---|---|---|---|---|---|---|---|---|---|
| Colloidal silicon dioxide | | | | | | 1.20 | 1.30 | 1.3 | 1.4 |
| Mg stearate | 1 | 1 | 1 | 1 | 1 | 1.2 | 1.3 | 1.3 | 1.4 |
| Total | 200.00 | 200.00 | 200.00 | 200.00 | 200.00 | 230.00 | 240.00 | 230.00 | 230.00 |

Methods of Preparation

For Examples I-V, Donepezil hydrochloride (Luna Chemicals), lactose (DMV Fonterra Excipients), Ethylcellulose (Hercules) and hydroxypropyl cellulose (Hercules) were mixed together in a mortar. A suitable amount of purified water was added to the mixture and wet granulation was carried out. The granules thus obtained were dried in an oven and then sieved to obtain the desired granulate size.

Granulate was mixed with lactose, HPMC (Colorcon), Carbopol (Lubrizol) and magnesium stearate (Merck) and then compressed into tablets comprising 20 mg Donepezil hydrochloride using a single punch tabletting machine.

For Examples VI-VIIIA, Donepezil hydrochloride (Neuland), lactose (DMV Fonterra Excipients), and hydroxypropyl cellulose (Hercules) were mixed in a V-processor. An aqueous solution of Kollidone in purified water was added to the mixture and wet granulation was carried out. The resulting granulate was further dried in a V-processor. Dried granules were milled using Glatt milling machine.

Granulate was mixed with microcrystalline cellulose (FMC), HPMC (Colorcon), Carbopol (Lubrizol), colloidal silicon dioxide (Cabot) and magnesium stearate (Merck) and then a KORSCH tabletting machine was used to form tablets, containing 20-23 mg Donepezil hydrochloride.

For Example VIII, tablets were then coated with OPADRY (Colorcon) in TAI-coater.

Dissolution Studies

The release profile of Donepezil hydrochloride from Donepezil hydrochloride 20 mg tablets of Examples 1-VII was determined by inserting six Donepezil hydrochloride tablets of each formulation into individual dissolution vessels, each containing 750 ml of 0.1 M hydrochloric acid. After 1 hour, the dissolution medium was changed by adding 250 ml of 0.2 M sodium phosphate. The pH was then adjusted to 6.8±0.05. The samples were continuously stirred with a VanKel paddle stirrer at 50 rpm.

Determination of the release was carried out using an automatic dissolution station. Samples were automatically drawn from each dissolution vessel through an appropriate filter into a flow cell. Samples analysis was performed automatically using a Cary UV system.

The percentage of release-controlling agents in each of the Examples tested is shown below:

| Example | HPMC K100 | Carbopol | HPMC K100M |
|---|---|---|---|
| I | 5 | 5 | 0 |
| II | 15 | 5 | 0 |
| III | 10 | 10 | 0 |
| IV | 5 | 15 | 0 |
| V | 5 | 10 | 1 |
| VI | 13 | 3 | 0 |
| VII | 13 | 4 | 0 |
| VIII | 13.6 | 4.5 | 0 |
| VIIIA | 10.1 | 8.6 | 0 |

Figure 1:
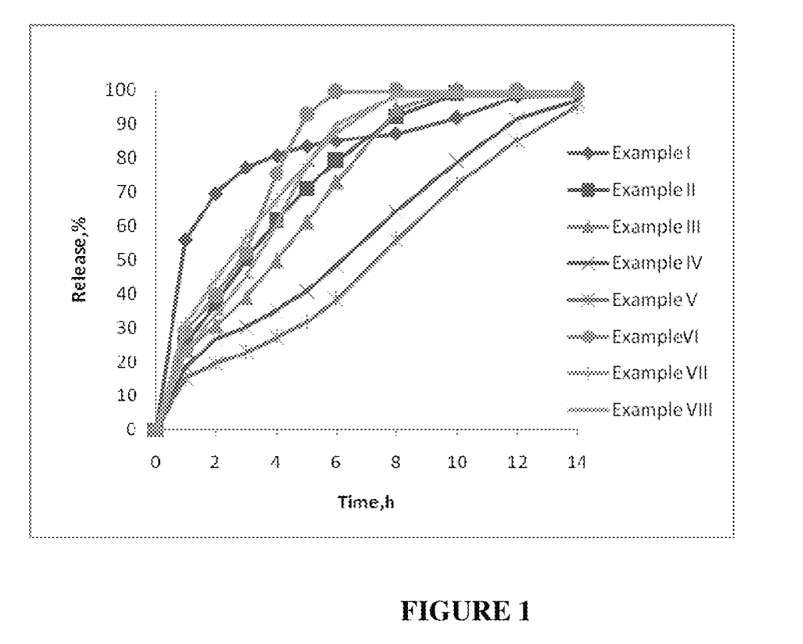
FIG. 1 shows the accumulative dissolution test results of formulations of Examples I-VIII comprising a combination of anionic gel-forming polymer (Carbopol) and non-ionic gel-forming polymer (HPMC) as release-controlling agents.

The accumulative dissolution test results of different formulations comprising a combination of anionic gel-forming polymer (Carbopol) and non-ionic gel-forming polymer (HPMC) as release-controlling agents are shown in FIG. 1 and in Table 1 below:

TABLE 1

| Time, h | Example I | Example II | Example III | Example IV | Example V | Example VI | Example VII | Example VIII | Example VIIIA |
|---|---|---|---|---|---|---|---|---|---|
| 0 | 0 | 0 | 0 | 0 | 0 | 0 | 0 | 0 | 0 |
| 1 | 55.93 | 25.39 | 23.42 | 18.46 | 15.24 | 28.97 | 31.36 | 23.10 | 18.26 |
| 2 | 69.59 | 37.04 | 30.43 | 26.71 | 19.47 | 39.43 | 44.27 | 33.87 | 20.50 |
| 3 | 77.14 | 50.30 | 38.99 | 30.09 | 22.69 | 52.10 | 56.52 | 44.90 | 25.10 |
| 4 | 80.66 | 61.41 | 49.64 | 35.17 | 27.05 | 75.17 | 67.75 | 60.23 | 31.38 |
| 5 | 83.28 | 71.04 | 61.12 | 40.65 | 31.65 | 92.66 | 78.00 | 77.75 | 39.75 |
| 6 | 85.06 | 79.11 | 72.87 | 48.38 | 38.22 | 99.50 | 87.62 | 90.00 | 50.67 |
| 8 | 87.16 | 92.23 | 94.24 | 64.43 | 55.91 | 99.82 | 98.89 | 98.30 | 70.65 |
| 10 | 91.73 | 98.90 | 100.00 | 78.86 | 72.22 | 99.86 | 99.32 | 98.30 | 86.50 |
| 12 | 97.94 | | | 91.36 | 85.05 | 99.82 | 99.52 | 98.30 | 97.93 |
| 14 | 98.48 | | | 96.75 | 95.04 | 100 | 99.82 | 98.30 | 100.83 |

Examples IX and X

Examples IX and X are based on a combination of an anionic gel-forming polymer (alginic acid) and non-ionic gel-forming polymer (HPMC) as release controlling agents.

| Materials | Example IX mg/tab | Example IX % | Example X mg/tab | Example X % |
|---|---|---|---|---|
| Donepezil HCl | 24.60 | 9.84% | 24.60 | 9.84% |
| Lactose | 126.05 | 50.42% | 126.05 | 50.42% |

-continued

| Materials | Example IX | | Example X | |
|---|---|---|---|---|
| | mg/tab | % | mg/tab | % |
| HPC L | 9.20 | 3.68% | 9.20 | 3.68% |
| Povidone K-30 | 3.45 | 1.38% | 3.45 | 1.38% |
| Total dry gran. | 163.30 | 65.32% | 163.3 | 57.30% |
| Avicel PH102 | 34.1 | 13.64% | 32.5 | 11.40% |
| HPMC K100 | | | 31.7 | 11.12% |

TABLE 2-continued

| Time, h | Example IX | Example X |
|---|---|---|
| 12 | 100.0 | 99.9 |
| 14 | 100.0 | 100.0 |

Examples XI-XX

Examples XI to XVIII are based on a combination of two non-ionic gel-forming polymers (HPMC), of different viscosities, as release controlling agents.

| Materials | XI mg/tab | XII mg/tab | XIII mg/tab | XIV mg/tab | XV mg/tab | XVI mg/tab | XVII mg/tab | XVIII mg/tab | XIX mg/tab | XX mg/tab |
|---|---|---|---|---|---|---|---|---|---|---|
| Donepezil HCl | 20 | 20 | 21.39 | 21.39 | 21.39 | 24.6 | 24.6 | 24.6 | 24.6 | 24.6 |
| Lactose | 122 | 122 | 98.75 | 98.75 | 98.75 | 126.05 | 126.05 | 126.05 | 126.05 | 126.05 |
| HPC L | 8 | 8 | 8 | 8 | 8 | 9.2 | 9.2 | 9.2 | 9.2 | 9.2 |
| Povidone K-30 | | | | | | 3.45 | 3.45 | 3.45 | 3.45 | 3.45 |
| Total dry gran. | 150.00 | 150.00 | 128.14 | 128.14 | 128.14 | 163.30 | 163.30 | 163.30 | 163.30 | 163.30 |
| Microcrystall. Cellulose | | | | 20 | 25.4 | 35 | 19.1 | 15.9 | 21.6 | |
| Lactise | 9 | 9 | 30.86 | 30.86 | 10.86 | | | | | |
| HPMC K100 | 30 | 34 | 38 | 30 | 36 | 37.5 | 37 | 45.0 | 46.9 | 45.0 |
| HPMC K15M | 10 | 6 | | | | 12.5 | 12.1 | 10.0 | 11.3 | 7.5 |
| HPMC K100M | | | 2 | 10 | 4 | | | | | |
| Povidone K-30 | | | | | | 10 | | 10 | 10 | 10 |
| Aerosil | | | | | | 1.3 | 1.3 | 1.3 | 1.3 | |
| Mg Stearate | 1 | 1 | 1 | 1 | 1 | 1.3 | 1.3 | 1.3 | 1.3 | 1.3 |
| Total | 200.00 | 200.00 | 200.00 | 200.00 | 200.00 | 250.00 | 250.00 | 250.00 | 250.00 | 250.00 |

-continued

| Materials | Example IX | | Example X | |
|---|---|---|---|---|
| | mg/tab | % | mg/tab | % |
| HPMC K15M | 12.1 | 4.84% | 11.4 | 4.00% |
| Alginic acid | 37.5 | 15.00% | 42.7 | 14.98% |
| Colloidal silicon dioxide | 1.5 | 0.60% | 1.7 | 0.60% |
| Mg Stearate | 1.5 | 0.60% | 1.7 | 0.60% |
| Total | 250.00 | 100.00% | 285.00 | 100.00% |

Tablets were prepared as described for Examples VI and VII above, with alginic acid used in place of Carbopol.

Figure 2:
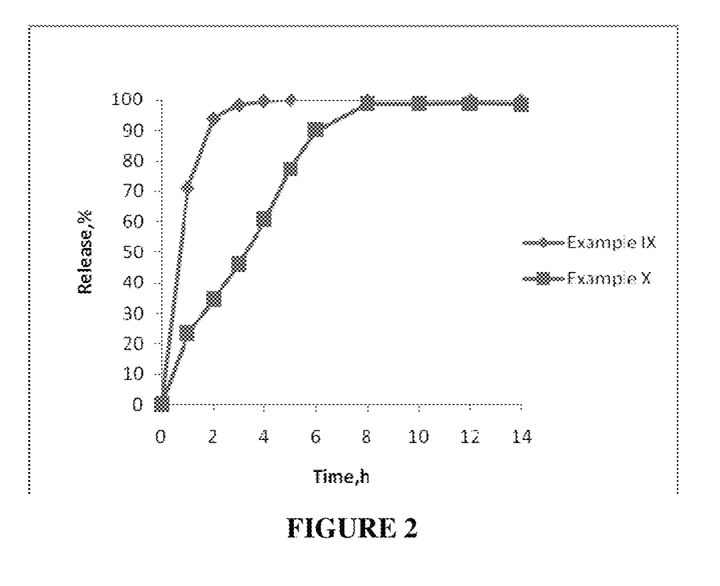
FIG. 2 shows the accumulative dissolution test results for the formulations of Examples IX and X.

Release profiles were determined as described above for Examples I-VII. The accumulative dissolution test results for the formulations of Examples IX and X are shown in FIG. 2 and in Table 2 below:

TABLE 2

| Time, h | Example IX | Example X |
|---|---|---|
| 0 | 0 | 0 |
| 1 | 71.1 | 30.2 |
| 2 | 93.9 | 41.0 |
| 3 | 98.3 | 50.3 |
| 4 | 99.5 | 59.8 |
| 5 | 100.0 | 71.8 |
| 6 | 100.0 | 83.7 |
| 8 | 100.0 | 97.9 |
| 10 | 100.0 | 99.6 |

Tablets for Examples XI-XIV were prepared as described for Examples I-V above; Examples XV-XX were prepared as described for Examples VI-VIII above;

Release profiles were determined as described above for Examples I-VIII.

The percentage of release-controlling agents in each of the Examples tested is shown below:

| Form. | HPMC K100 | HPMC K15M | HPMC K100M |
|---|---|---|---|
| XI | 15 | 5 | 0 |
| XII | 17 | 3 | 0 |
| XIII | 19 | 0 | 1 |
| XIV | 15 | 0 | 5 |
| XV | 18 | 0 | 2 |
| XVI | 15 | 5 | 0 |
| XVII | 14.8 | 4.8 | 0 |
| XVIII | 18 | 4 | 0 |
| XIX | 18.9 | 4.5 | 0 |
| XX | 18 | 3 | 0 |

Figure 3:
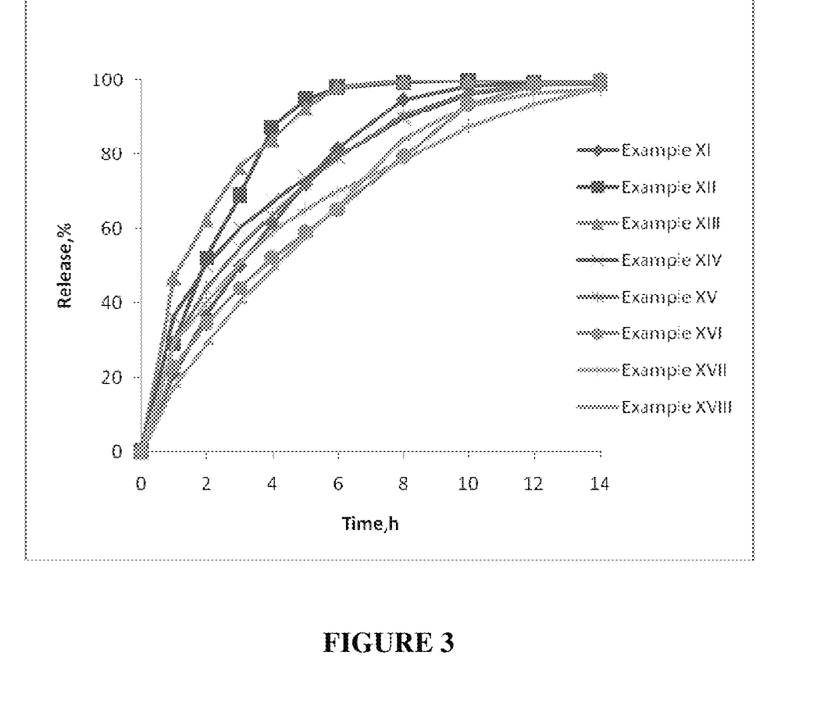
FIG. 3 shows the accumulative dissolution test results for the formulations of Examples XI-XVIII.

The accumulative dissolution test results for the formulations of Examples XI-XX are shown in Table 3 below; results for Examples XI-XVIII are further shown in FIG. 3.

TABLE 3

| Time, h | XI | XII | XIII | XIV | XV | XVI | XVII | XVIII | XIX | XX |
|---|---|---|---|---|---|---|---|---|---|---|
| 0 | 0 | 0 | 0 | 0 | 0 | 0 | 0 | 0 | 0 | 0 |
| 1 | 20.95 | 29.19 | 46.91 | 36.49 | 29.36 | 22.76 | 29.49 | 17.59 | 18.42 | 19.88 |
| 2 | 36.76 | 52.24 | 62.37 | 50.13 | 43.79 | 34.54 | 40.06 | 29.07 | 30.30 | 33.33 |
| 3 | 49.97 | 68.87 | 76.58 | 60.05 | 54.87 | 44.15 | 50.63 | 40.22 | 39.58 | 43.67 |
| 4 | 61.39 | 87.29 | 84.06 | 67.25 | 63.79 | 52.06 | 59.13 | 49.15 | 47.3 | 53.17 |
| 5 | 71.92 | 94.75 | 92.36 | 73.50 | 72.00 | 58.92 | 65.14 | 57.85 | 54.42 | 62.62 |
| 6 | 81.83 | 97.87 | 98.18 | 79.49 | 79.25 | 65.33 | 70.02 | 66.25 | 61.35 | 72.13 |
| 8 | 94.77 | 99.26 | 99.79 | 89.70 | 90.47 | 79.34 | 78.55 | 84.11 | 75.00 | 92.40 |
| 10 | 98.37 | 99.78 | 99.84 | 96.13 | 96.45 | 93.38 | 87.45 | 93.2 | 88.37 | 100.22 |
| 12 | 99.12 | 99.37 | 99.90 | 98.64 | 98.90 | 98.60 | 93.74 | 96.42 | 96.58 | 101.62 |
| 14 | 99.18 | 99.43 | 99.90 | 99.60 | 98.90 | 100 | 97.70 | 97.48 | 99.27 | 101.48 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A sustained-release formulation comprising an acetylcholinesterase inhibitor, wherein the acetylcholinesterase inhibitor is donepezil or a pharmaceutically acceptable salt thereof, wherein the release rate of the acetylcholinesterase inhibitor is controlled by two non-ionic gel-forming polymers which are a combination of a low viscosity grade hydroxypropyl methylcellulose polymer (low viscosity grade HPMC polymer) and a high viscosity grade hydroxypropyl methylcellulose polymer (high viscosity grade HPMC polymer), the formulation comprising:
   (a) donepezil or a pharmaceutically acceptable salt thereof in a concentration of about 10% (w/w) of the total formulation;
   (b) the low viscosity grade HPMC polymer in a concentration in the range of from about 11% to about 19% (w/w) of the total formulation;
   (c) the high viscosity grade HPMC polymer in a concentration in the range of from about 3% to about 5% (w/w) of the total formulation; and
   (d) at least one excipient selected from the group consisting of a filler, a binder, a disintegrant, and a glidant.

2. The formulation of claim 1, wherein the pharmaceutically acceptable salt of donepezil is donepezil hydrochloride.

3. The formulation of claim 1, wherein the filler is selected from the group consisting of lactose, glucose, fructose, sucrose, dicalcium phosphate, a sugar alcohol, corn starch, potato starch, sodium carboxymethylcellulose, ethylcellulose, cellulose acetate, hydroxypropyl methylcellulose acetate succinate, cellulose acetate phthalate, hydroxypropyl methyl cellulose phthalate, polyvinyl acetate phthalate, poly(methacrylic acid, methyl methacrylate) 1:1, poly(methacrylic acid, ethyl acrylate) 1:1, alginic acid, sodium alginate, and a mixture thereof.

4. The formulation of claim 1, wherein the binder is selected from the group consisting of polyvinyl pyrrolidone, a copolymer of polyvinyl pyrrolidone and polyvinyl acetate, low molecular weight hydroxypropyl cellulose, low molecular weight carboxy methyl cellulose, ethylcellulose, gelatin, polyethylene oxide, acacia, dextrin, magnesium aluminum silicate, starch, polymethacrylate, hydroxvpropyl methylcellulose acetate succinate, cellulose acetate phthalate, hydroxypropyl methyl cellulose phthalate, polyvinyl acetate phthalate, poly(methacrylic acid, methyl methacrylate) 1:1, poly(methacrylic acid, ethyl acrylate) 1:1, alginic acid, sodium alginate, and a mixture thereof.

5. The formulation of claim 1, wherein the disintegrant is selected from the group consisting of low-substituted carboxymethyl cellulose sodium, crospovidone, sodium carboxymethyl starch, cross-linked sodium carboxymethyl cellulose, pregelatinized starch, microcrystalline cellulose, water insoluble starch, calcium carboxymethyl cellulose, low substituted hydroxypropyl cellulose, magnesium silicate, aluminum silicate, and a mixture thereof.

6. The formulation of claim 1, wherein the glidant comprises at least one of silicone dioxide and magnesium stearate.

7. The formulation of claim 1, wherein the low viscosity grade HPMC polymer is HPMC K100 and the high viscosity grade HPMC polymer is HPMC K100M.

8. The formulation of claim 1, wherein the low viscosity grade HPMC polymer is HPMC K100 and the high viscosity grade HPMC polymer is HPMC K15M.

* * * * *